(12) United States Patent
Melzer et al.

(10) Patent No.: US 7,766,932 B2
(45) Date of Patent: Aug. 3, 2010

(54) VESSEL FILTER

(75) Inventors: Andreas Melzer, Mülheim an der Ruhr (DE); Gregor Schaefers, Bottrop (DE)

(73) Assignee: aMRIs Patente GmbH, Castrop-Rauxel (DE)

( * ) Notice: Subject to any disclaimer, the term of this patent is extended or adjusted under 35 U.S.C. 154(b) by 0 days.

(21) Appl. No.: 10/540,786

(22) PCT Filed: Dec. 12, 2003

(86) PCT No.: PCT/DE03/04199

§ 371 (c)(1),
(2), (4) Date: Sep. 21, 2005

(87) PCT Pub. No.: WO2004/053512

PCT Pub. Date: Jun. 24, 2004

(65) Prior Publication Data

US 2006/0058832 A1    Mar. 16, 2006

(30) Foreign Application Priority Data

Dec. 12, 2002 (DE) .............................. 102 58 708

(51) Int. Cl.
*A61M 29/00* (2006.01)
*A61B 5/05* (2006.01)

(52) U.S. Cl. ...................... 606/200; 600/411
(58) Field of Classification Search ............... 606/200; 600/410, 411, 421–423
See application file for complete search history.

(56) References Cited

U.S. PATENT DOCUMENTS

| | | | | |
|---|---|---|---|---|
| 4,655,219 A | * | 4/1987 | Petruzzi | 606/206 |
| 5,234,458 A | * | 8/1993 | Metais | 606/200 |
| 5,540,712 A | * | 7/1996 | Kleshinski et al. | 623/1.19 |
| 5,938,645 A | * | 8/1999 | Gordon | 604/264 |
| 5,968,071 A | * | 10/1999 | Chevillon et al. | 606/200 |
| 6,156,061 A | * | 12/2000 | Wallace et al. | 623/1.11 |
| 6,224,612 B1 | * | 5/2001 | Bates et al. | 606/114 |
| 6,238,412 B1 | * | 5/2001 | Dubrul et al. | 606/200 |

(Continued)

FOREIGN PATENT DOCUMENTS

EP    1092985 A1    10/1998

(Continued)

OTHER PUBLICATIONS

Bartels et al., "Improved Lumen Visualization n Metallic Vascular Implants by Reducing RF Artifacts," Magenetic Resonance in Medicine, Wiely, vol. 47, No. 1, Jan. 2002, pp. 171-180, XP002277498, USA, ISSN: 0740-3194.

(Continued)

*Primary Examiner*—Todd E Manahan
*Assistant Examiner*—Lindsey Bachman
(74) *Attorney, Agent, or Firm*—Woodard, Emhardt, Moriarty, McNett & Henry LLP

(57) ABSTRACT

The invention relates to a vessel filter comprising at least one conductor loop (21) which forms the inductance of an electric resonance circuit. According to the invention, the conductor loop (21) forms the vessel filter or parts of a vessel filter. The invention provides a vessel filter which is characterized by good mechanical properties, especially a high degree of flexibility and stability, offering good representability in MR imaging systems.

28 Claims, 10 Drawing Sheets

U.S. PATENT DOCUMENTS

| | | | |
|---|---|---|---|
| 6,540,767 B1 * | 4/2003 | Walak et al. | 606/200 |
| 6,558,404 B2 * | 5/2003 | Tsukernik | 606/198 |
| 6,847,837 B1 * | 1/2005 | Melzer et al. | 600/421 |
| 7,011,672 B2 * | 3/2006 | Barbut et al. | 606/200 |
| 2001/0031980 A1 * | 10/2001 | Wensel et al. | 606/200 |
| 2001/0039431 A1 * | 11/2001 | DeVries et al. | 606/200 |
| 2003/0208227 A1 * | 11/2003 | Thomas | 606/200 |

FOREIGN PATENT DOCUMENTS

| | | |
|---|---|---|
| WO | WO 99/19739 | 4/1999 |

OTHER PUBLICATIONS

Busch, M. et al., "A Physical Explanation of Active MRI Stents (aMRIs) and First "In Vitro" and "In Vivo" Results," ISMRM Tenth Meeting PRoceedings, May 18, 2002, XP002277512, Honolulu, HI, USA.

Schaefers G. et al., "New Vena Cava Filter (VCF) with Integrated Inductively Coupled Resonator for MR Micro Imaging," ISMRM Tenth Meeting Proceedings, May 18, 2002, XP002277496, Honolulu, HI, USA.

Siskin G.P., Bartholomew, K., "Inferior Vena Cava Filters", Dec. 6, 2002, pp. 1-25, XP002277497, http://www.emedicine.com/radio/topic762.htm>, retrieved on Apr. 20, 2004.

* cited by examiner

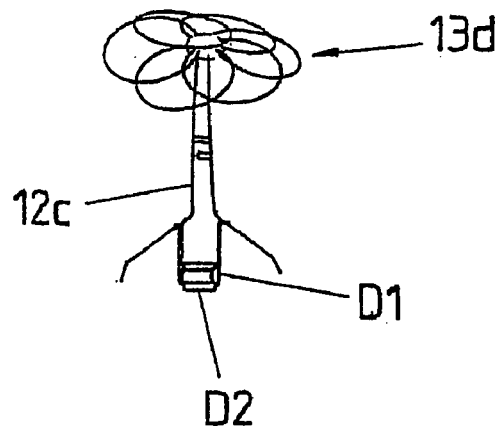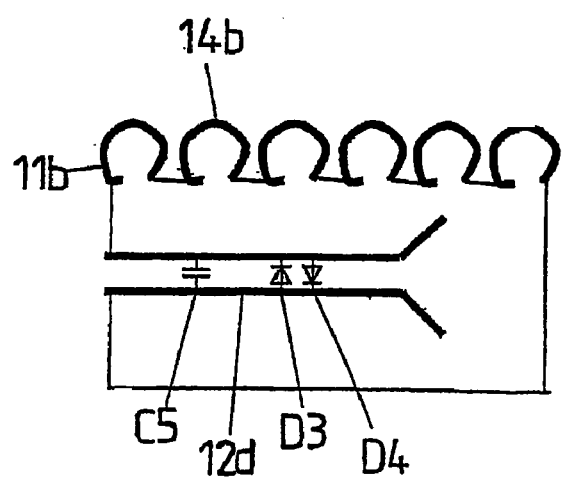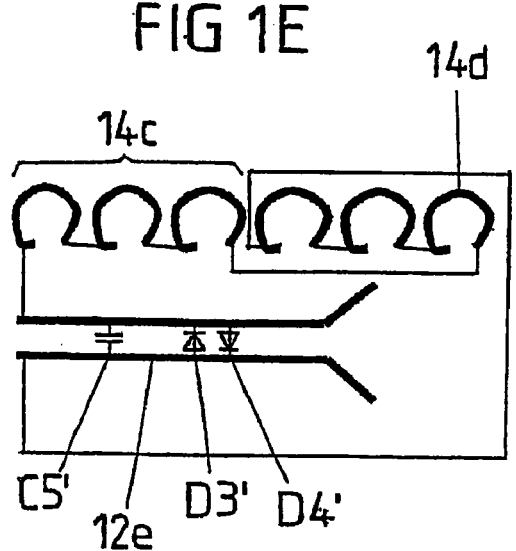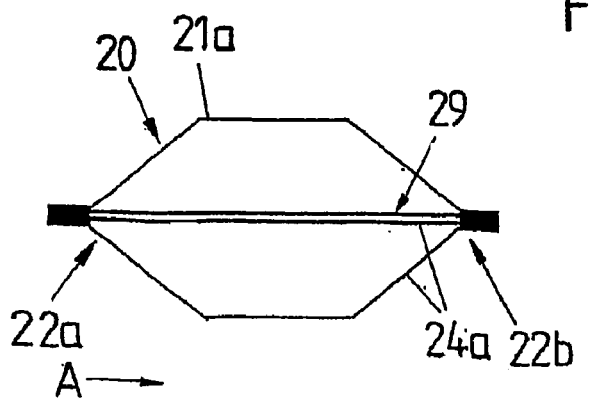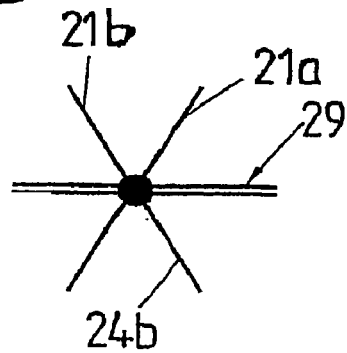

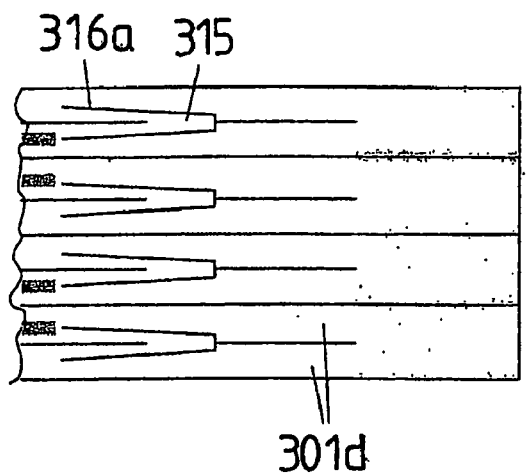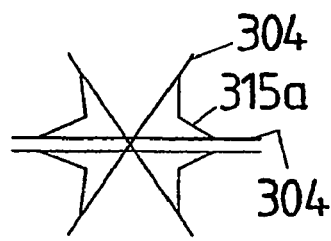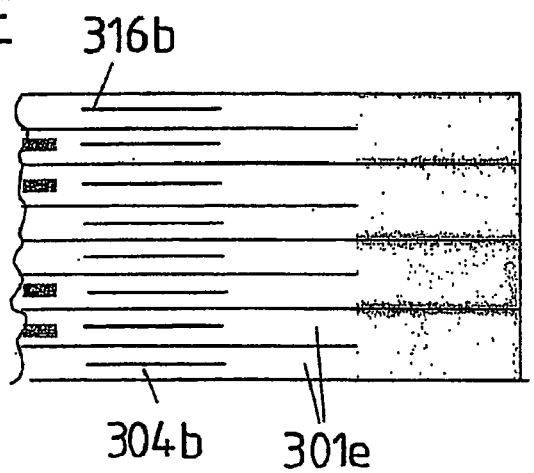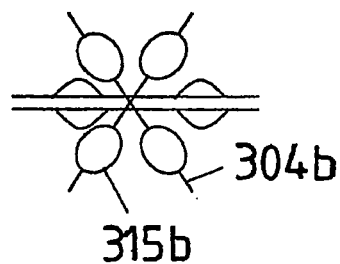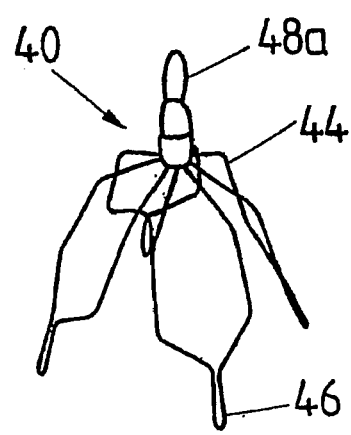

VESSEL FILTER

CROSS-REFERENCES TO RELATED APPLICATIONS

This application is a National Stage of International Application PCT/DE2003/004199, filed Dec. 12, 2003. Applicant claims foreign priority to benefits under 35 U.S.C. 119(a)-(d) of the following foreign application for patent: German Application No. 102 58.708.6, filed Dec. 12, 2002, which is hereby incorporated by reference in its entirety.

BACKGROUND OF THE INVENTION

The invention concerns a vessel filter that includes a conductor loop that forms the inductance of an electrical resonance circuit.

Vessel filters are structures that are inserted into traversed veins and arteries of the human or animal body, especially the inferior vena cava, in order to prevent penetration of blood clots or sclerotic vascular material into organs of the body, especially the lungs and brain.

For application, vessel filters are generally mounted or fastened in the unexpanded state on a wire to be introduced to the body or brought to the target location of implantation in a catheter via a surgical vein access and then deployed. The diameter of the vessel filter is then enlarged, so that the filter presses against the vessel wall and is fastened there.

There is a requirement, for displaying of vessel filters by imaging methods during implantation and for later functional control or removal. Recently, magnetic resonance (MR) imaging systems have increasingly gained importance in medical diagnosis. Interventional and minimally invasive techniques, like puncture, catheterization and surgical procedures, in particular, are conducted under MR tomographic control. Depiction and position determination of a vessel filter in an MR imaging system, however, is difficult. Metal vessel filters are only visible as an artifact, and vessel filters made of plastic are scarcely visible at all because of their fine structure in the MR image.

It is known from WO-A1 99/19739 for a clear and signal-intensive representation of a medical device in an MR image to integrate in this device an oscillating circuit that generates an altered signal response in a locally limited region or around the medical device, which is depicted with location resolution. The resonance frequency of the oscillating circuit is essentially equal to the resonance frequency of the emitted high-frequency radiation of the MR imaging system. The to oscillating circuit in the medical device can then be made of the same material. In one variant, the oscillating circuit is integrated in the medical device, so that the inductance appears together with it during deployment of the device.

MR-active vessel filters are also known from the literature. These instruments consist of a filter part and a separate conductor loop wound around the filter. After introduction into the body, the conductor loop and vessel filter can be deployed.

A shortcoming in vessel filters of this type is the fact that they consist of a basic framework for the filter function onto which a conductor loop must be wound in order to provide the device with the desired MR activity. The connection of two components has an adverse effect on the mechanical stability of the vessel filter.

The task of the present invention is to provide a vessel filter characterized by good mechanical properties, especially a high degree of flexibility with simultaneous stability, and one that is readily viewable in an MR imaging system.

This task is accomplished according to the invention by a vessel filter with the features of a conductor loop, forming the inductance of an electrical resonance circuit. Preferred and advantageous embodiments of the invention are mentioned in the dependent claims. The conductor loop forms the vessel filter or at least parts of the vessel filter. The concept according to the invention therefore lies in using only one structure, namely, a conductor loop, both to form the actual filter and for the inductance. In combination with a capacitance, a resonance circuit is therefore provided.

In a preferred embodiment, the vessel filter forms several resonance circuits, each with at least one conductor loop. Because of this, a situation can be achieved in which the vessel filter can be operated and detected at several different MR frequencies. It can also be prescribed that several resonance circuits be coupled to each other.

In an advantageous variant, the vessel filter forms at least one integrated circuit coupled to the resonance circuits so that they can be adjusted or tuned by the integrated circuit in addition to the resonance circuit or the resonance circuits. The integrated circuit permits external influencing of the resonance frequency with to adjustment or tuning, for example, by switching on and/or switching off the inductive or capacitive elements of the oscillating circuit. The power supply of the integrated oscillating circuit can occur through a small power supply (for example, battery), or also by inductive coupling of energy from an electromagnetic field.

In an advantageous variant, the vessel filter has spacers and/or insulators that keep the individual sections of the conductor loops at a spacing from each other and/or insulate them relative to each other. Because of this, short circuits between individual conductor windings are prevented. In addition, the insulators, in a particularly advantageous variant, are simultaneously a part of the internal capacitance in conjunction with at least one conductor loop. This develops by a connection and simultaneous insulation of the ends with an insulator (for example, polymer, ceramic, composite) that represents a dielectric and forms at least one capacitance (capacitor) connected electrically in the network with at least two conductors separated by the insulator.

The conductor loop is advantageously enclosed by a non-conductor, especially plastic and/or ceramic. This serves for increased the lifetime of the vessel filter by increased mechanical stability and its disturbance-free function. In a particularly preferred variant, insulation serves to reduce and regulate the parasitic capacitance, wherein the insulation can also be used to tune the oscillating circuit, i.e., for fine adjustment of the resonance frequency. Fine adjustment is also possible by deformation of the filter and therefore a change in inductance. This can be determined primarily by expansion or compression or by limiting vessel diameter. The vessel filter according to the invention therefore gets by in its simplest variant without an additional capacitance, since a combination of an internal and parasitic capacitance is sufficient for its function. Insulation also ensures that no electrical contact to other conductor loops is present between the ends of the individual conductor loops which would alter the prescribed inductance by a short circuit.

In an advantageous variant of the vessel filter according to the invention, the resonance circuit has a resonance frequency, especially in the high-frequency range, which corresponds to the frequency of an external magnetic field, especially an MR tomograph (MRT). Implantation and function of the vessel filter can therefore be observed by imaging MR methods. However, it is also conceivable to provide an to oscillating circuit with a resonance frequency in a different frequency range.

In an advantageous variant, the conductor loop has at least one electrically nonconducting material on whose surface at least one conducting material is applied, especially gold, platinum, tantalum and/or conducting alloys. The choice of specially conducting materials, for example, gold, improves the formation of resonance. Several layers of an insulator and conductor can also be applied to the conductor loop.

The conductor loop of the vessel filter is advantageously designed so that it can be deployed. The resonance circuit can preferably be formed during and/or after implantation in a biological medium. The vessel filter can therefore be implanted in folded form and deployed during implantation or only at its target location. This permits implantation starting from small veins or arteries in the periphery of the body. However, in principle, it is also possible to form it before transplantation.

In an advantageous variant, the vessel filter according to the invention has several conductor loops. This permits greater flexibility in configuring the vessel filter and a higher filter function. In addition, the resonance can be further improved by the presence of several conductor loops.

"Conductor loop" is understood to mean a conductor consisting of one piece. "Conductor loop winding" is understood to mean a section of the conductor loop that is brought into a specific shape, in which the straight shape is also included.

In another advantageous variant, the so-called umbrella filter, the vessel filter has several conductor loop windings guided so that the conductor loop forms an elongated base that is closed on at least one side with a screen-like filter cage. This variant leads to a particularly good filter effect.

The term "filter cage" is used to denote the part of the vessel filter that contains the conductor loop windings, which, owing to the fact that they are brought together on at least one long side of the filter, are in a position to retain thrombi of clotted blood or sclerotic material in the blood vessel.

In another advantageous variant, the so-called diamond filter, the vessel filter has several conductor loop windings guided so that the largest spacing of the loop windings from each other is present in the center and tapers to at least one long side. In a particularly advantageous variant, the conductor loop windings taper to two sides, which improves the filter effect. Independently of the number of filter cages, the advantage of this variant lies in the fact that a large part of the conductor loop windings lies against the vessel wall, which leads to good and permanent and tilting-free fastening to the vessel wall, which can additionally be supported by anchoring in the vessel wall with hooks. In addition, this type of filter permits good illumination of the filter interior in the MR method.

In another advantageous variant, also referred to as a tulip filter, the vessel filter has at least one conductor loop winding that runs together in a filter cage on one side of the filter and extends leg-like on the other side of the filter. A filter forming at least one extension that serves for connection of the filter to a vessel wall is particularly preferred. With particular advantage, the regions of the conductor loop winding adjacent to the extension are at a limited spacing from each other. It is particularly preferred that the adjacent regions of the conductor loop winding in the extension be connected to each other without an intermediate space, especially by welding, soldering or pressing. However, they can also consist of one piece, i.e., the continuation is formed by a one-piece part connected to the conductor loop winding. Because of this, the contact surface of the vessel filter with the vessel wall is minimized and a situation is achieved in which the filter can be removed without rupturing the vessel wall, since the intima grows pocket-like around the extension.

It is particularly advantageous if the extension points in the direction of blood flow of the vessel in which the filter is arranged. Because of this, anchoring in the vessel wall and intima of the vessel is achieved, which optimally counteracts the flow force of the blood. To remove the vessel filter, the filter is initially moved against the direction of blood flow, in order to remove the extension from the intima pockets. After collapse of the filter, it can be removed without problem from the body.

It is also advantageous if the extension points in the direction of the vessel wall. This also requires a fixed anchoring in the vessel wall, both by growing of the intima around the extension and by concentration of the pressure force on this extension. Anchoring can be improved by additional hooks. An improved anchoring can be improved by a sealing coating with greater depth of roughness.

It is particularly preferred that the extensions be arranged moveably against the braces, for example, of the tulip filter. The resonance frequency of the filter also depends on its diameter. During deployment of this variant of the vessel filter, the extensions shift relative to the braces as a function of the vessel diameter, which determines the width of deployment. Because of the moveability, any change in resonance frequency is compensated by a change in filter diameter so that the resonance frequency remains almost constant as a result. Imaging in MR therefore remains optimally independent of vein diameter. Anchoring in this case is assumed by the fixed brace and is possible by anchoring with hooks.

In another advantageous variant, the so-called low-pass birdcage filter, the vessel filter contains at least two foldable conductor loops, especially guided in zigzag fashion, in which one conductor loop forms a capacitance at least one reversal point with at least another conductor loop or permits connection of an external capacitance, and the reversal points of at least one of the conductor loops on one side have a smaller spacing relative to each other than on the other side, and, in particular, form a filter cage.

In another advantageous variant, the so-called high-pass birdcage filter, the vessel filter contains at least two conductor loops guided in closed vessel filters in the longitudinal direction and connected on at least one end to another conductor loop by a capacitance.

Anchoring of the birdcage filter in the vessel wall can be produced by hooks. One means of connection for coupling between filters and catheters can also be a filter component.

In both cases, a very homogeneous magnetic field is created by the arrangement of inductances and capacitances according to the principle of a birdcage coil, which permits excellent. MR illumination and therefore intravascular imaging even of the immediate vicinity of the filter.

The design of a double-filter is particularly advantageous. This is understood to mean a vessel filter that forms a filter cage on both opposite long sides. Double-filters can be implemented, for example, in the variants of the umbrella, diamond and birdcage filter. The advantage of a double-filter lies in better illumination in the MR image with simultaneously optimized filter effect.

The individual windings of the conductor loops are advantageously arranged in the longitudinal direction of the vessel filter. This leads to a particularly mechanically to stable filter and also leads to good and permanent connection with the vessel wall. This is necessary, in particular, for a vessel filter permanently remaining in the vessel.

In an advantageous variant, the vessel filter according to the invention has at least one brace connected to the conductor loop. These braces improve the mechanical stability of the filter and increase the filter effect. At the same time, they can also serve to anchor it in the vessel wall. The braces can be fastened on their ends with plastic sealant or a crimping sleeve mounted in insulated fashion.

In another advantageous variant, the braces are conducting and are connected conducting to the conductor loop. Because of this, during use of conductor loop material, production is possible from only one piece. They therefore become part of the coil and can improve the resonance.

In a particularly preferred variant, the individual braces are connected moveably to the individual conductor loop windings.

A vessel filter containing braces made of bioresorbable material is particularly advantageous. After the braces are broken down by the body, the vessel filter has fewer connections to the veins or arteries than right before implantation. The vessel filter therefore sits loosely against the tissue. This permits easy removal of the implant from the body.

In an advantageous variant, the vessel filter forms at least one semiconductor element, especially a diode and/or a transistor and/or an integrated circuit. This diode permits tuning of the resonance frequency which leads to better detectability in an MR system. The transistor can also tune the oscillating circuit and be controlled via an additional inductive switching coil.

The conductor loop is advantageously formed from a material piece, especially a tube, a wire or electrically-conducting plastic. This permits simple and cost-effective production.

It is advantageous to produce the conductor loop by repeated lengthwise cutting of a tube, especially a Nitinol tube, and then expansion. It is particularly advantageous to guide the conductor loop on the sides in meander-like fashion. With this type of production, insulation of the conductor parts from each other is particularly facilitated.

The ends of the conductor loop windings are preferably joined by welding, gluing, clamping, sealing and/or shape-mating, especially by thermally initiated shrinkage of a cylinder from a shape-memory material.

In another advantageous variant, the vessel filter contains at least one conductor loop winding, provided with at least one hook. These hooks permit additional fastening of the filter in the vessel wall and therefore prevent filter wandering.

The vessel filter advantageously has at least one connection device, for example, a lug, for coupling with a device for introduction and/or extraction of the filter, for example, a catheter. This permits the operator's easy handling of the vessel filter during implantation and/or extraction.

The vessel filter also preferably contains at least one means for braking of the filter during introduction to the body. The braking device is preferably formed by a region of increased diameter or by a local constriction of the catheter. This permits the operator greater manual control and therefore more precise implantation in the blood vessel.

It is particularly advantageous, if the connection device is the braking device.

BRIEF SUMMARY OF THE INVENTION

A vessel filter according to the present invention includes a conductor loop, forming the inductance of an electrical resonance circuit. The conductor loop forms the vessel filter or at least parts of the vessel filter. The concept according to the invention therefore lies in using only one structure, namely, a conductor loop, both to form the actual filter and for the inductance. In combination with a capacitance, a resonance circuit is therefore provided.

BRIEF DESCRIPTION OF THE SEVERAL VIEWS OF THE DRAWINGS

FIG. 1 shows a view of a vessel filter in the variant of the umbrella filter.

FIG. 1c shows an umbrella filter with a filter cage and two diodes.

FIG. 1d shows a circuit diagram of an umbrella filter for the vertical MRT main magnetic field.

FIG. 1e shows a circuit diagram of an umbrella filter for the vertical and horizontal MRT main magnetic field.

FIG. 2 shows a depiction of a diamond filter, designed as a double-filter.

FIG. 2a shows a diamond filter in the front view.

FIG. 2b shows a diamond filter in the side view.

FIG. 3 shows the production of a vessel filter in the variant of the diamond filter.

FIG. 3c shows an alternative cutting pattern with additional braces for increasing the filter function of the diamond filter.

FIG. 3d shows the cutting pattern of FIG. 3c in a side view in the expanded state.

FIG. 3e shows another alternative cutting pattern with additional braces for increasing the filter function of the diamond filter.

FIG. 3f shows the cutting pattern of FIG. 3e in a side view around the expanded state.

FIG. 4 shows a tulip filter.

FIG. 4a shows a tulip filter in compact form.

FIG. 5 shows a birdcage filter.

FIG. 6 shows a coupling between the guide wire/catheter and vessel filter.

DETAILED DESCRIPTION OF THE INVENTION

Figure 1A:
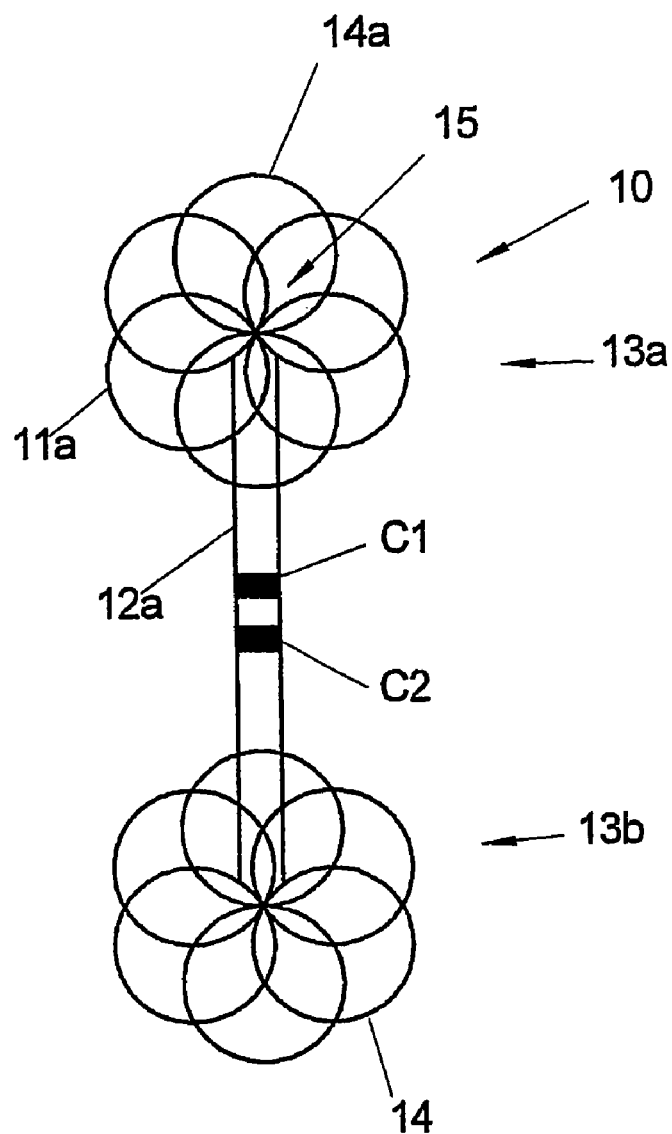
FIG. 1a shows an umbrella filter, designed as a double-filter.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

In FIGS. 1a-1e, vessel filters are shown in the variant of a so-called umbrella filter. The umbrella filter 10 in FIG. 1a is designed as a double-filter in which a conductor loop 11a forms an elongated base 12a and, on both long sides, base 12a is guided, so that two filter cages 13a, 13b are formed, each of which consists of a number of conductor loop windings 14, 14a arranged in a circle. At the center of base 12a, two capacitances C1, C2 are formed, or provided as separate parts. The entire vessel filter, apart from any additional capacitances, is made from a conductor loop 11a.

In the center 15 of filter cages 13a, 13b, the individual conductor loop windings 14, 14a are separated from each other by insulators and spacers (not shown separately) in order to avoid short circuits and permit resonance formation.

Other geometries of the filter cages are also possible. The design of the edges can thus improve adaptation to a vessel wall. The filter cages 13a, 13b can be formed, for example, as circular cutouts. By formation as triangles or polygons, anchoring can be improved by increasing the pressure on the contact sites with the vessel wall.

Figure 1B:
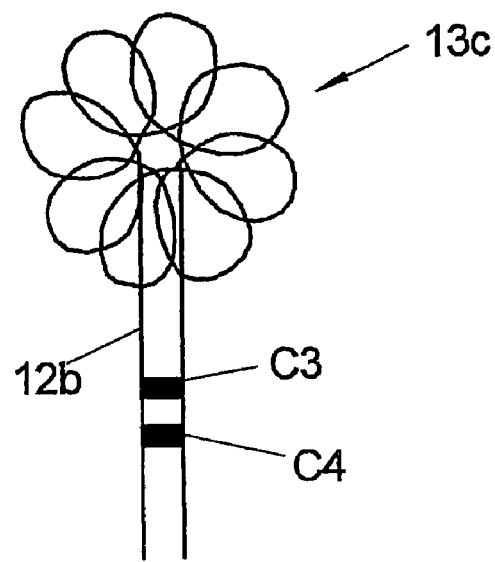
FIG. 1b shows an umbrella filter with a filter cage.

An umbrella filter that forms only one filter cage 13c is shown in FIG. 1b. Here again, two capacitances C3, C4 are formed on base 12b or provided as separate parts.

In FIG. 1c, two diodes D1, D2 are mounted on the end of base 12c of an umbrella filter on the side facing away from filter cage 13d. The optionally present diodes permit tuning of the resonance frequency, as described in WO-A1 99/19739.

A circuit diagram of an umbrella filter according to FIGS. 1a-1c is shown in FIG. 1d. Both a capacitance C5 and two diodes (D3, D4) are arranged within base 12d. A conductor loop 11b, for example, forms six conductor loop windings 14b in order to form the filter cage. Whereas the conductor loop 11b in FIG. 1d is guided so that the filter is only actively visible in the vertical MRT main magnetic field, the circuit depicted in FIG. 1e is guided so that the filter shows resonance both in the horizontal and vertical magnetic fields. For this purpose, after series connection of the first conductor loop windings 14c, contact is made to the last conductor loop winding 14d, and all still unconnected conductor loop windings are connected in series to each other up to the center. Generally speaking, the same direction of winding of the conductor loops is ensured referring to the employed spin magnetization. Within base 12e, both a capacitance C5' and two diodes (D3', D4') are arranged.

The conductor loop forms an inductance that produces an oscillating circuit with the capacitance. The oscillating circuit can be excited by the high-frequency field of an MR imaging system so that improved viewing occurs in the MR image. The optionally present diodes permit tuning of the resonance frequency, as described in WO-A1 99/19739, entitled MR IMAGING METHOD AND MEDICAL DEVICE FOR USE IN METHOD, by inventors Melzer and Busch, filed Apr. 22, 1999, which is hereby incorporated by reference in its entirety.

A vessel filter, designed as a so-called diamond filter 20, is shown in FIG. 2a. The diamond filter 20 consists of a conductor loop 21a forming several conductor loop windings 24a. The largest spacing of the conductor loop windings 24a from each other is present lengthwise in the center, but some conductor loop windings 24a can also be guided as double-windings 29 parallel at limited spacing from each other.

Along both long sides, a tapering occurs so that a double-filter with two lateral filter cages 22a, 22b is formed. It should be noted that other geometries of the conductor track(s) with edges and curvatures are possible in order to reduce contact with the vessel wall and increase the pressure on the vessel wall by reducing the contact surface.

The conductor loop 21b that forms several conductor loop windings 24b is shown in FIG. 2b in a side view in the direction of arrow A of FIG. 2a. Some conductor loop windings 24b are guided parallel with limited spacing from each other as double-windings 29. A first conductor loop 21a and a second conductor loop 21b are shown. Versions are also possible that contain more than one conductor loop and can also form more than one oscillating circuit.

Figure 2C:
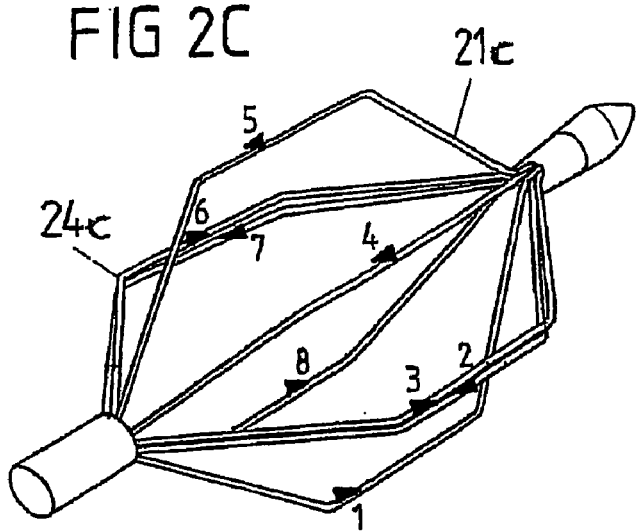
FIG. 2c shows a circuit plan of a diamond filter.
Figure 2D:
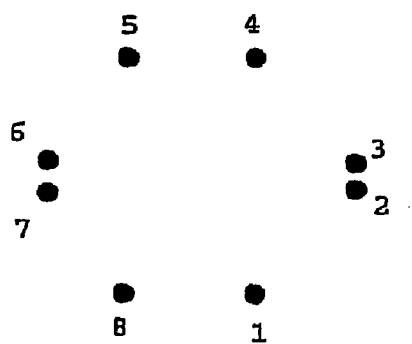
FIG. 2d shows a cross-sectional circuit plan of a diamond filter.

FIG. 2c shows the windings of conductor loop 21c of the diamond filter. Schematically, one direction of the alternating current flow is shown by arrows on the conductor loop windings 24c. The diamond filter of FIG. 2c is shown schematically in a corresponding cross section in FIG. 2d. The current flows in FIGS. 2c and 2d, starting with 1 back via 2, to 6 and back via 5, to 3 and back via 4, to 8 and back via 7.

The flow can also occur as follows with fewer intersection points of the conductors with an advantage for production: starting at 1 back via 2, to 3 and back via 4, to 8 and back via 7, to 6 and back via 5.

Figure 2E:
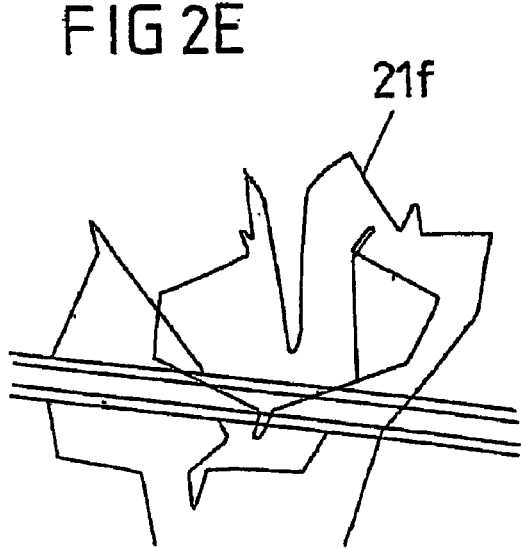
FIG. 2e shows a wire winding of a diamond filter.

A bent diamond filter is shown in FIG. 2e. The filter consists of only one conductor loop 21f, whose windings are apparent.

Figure 2F:
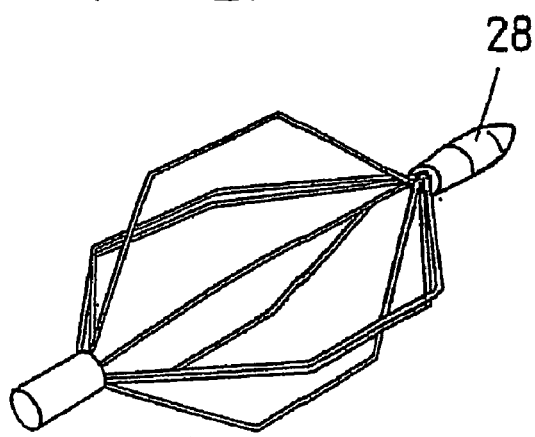
FIG. 2f shows a diamond filter with a connection device.

FIG. 2f shows a diamond filter with a connection device 28 made of an electrically-conducting material on a tapered end that can be fastened without a glue connection, for example, by crimping or by heat shrinkage of a shape-memory alloy. It is also possible to apply two connection devices to the filter. The conductor loop ends are enclosed with a dielectric, especially epoxy resin, which is not visible here. Because of this, formation of capacitances occurs during joining of the conductor loop windings.

Figure 2G:
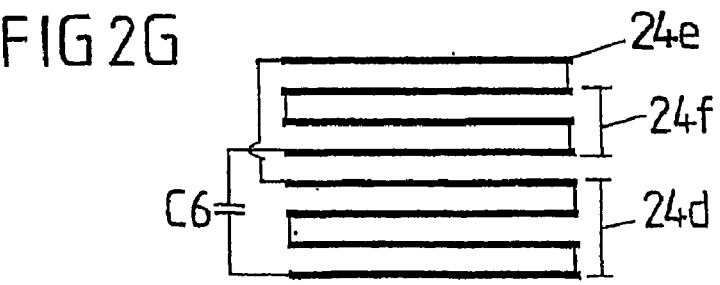
FIG. 2g shows a circuit diagram of a diamond filter for the vertical and horizontal MRT main magnetic field.

An electrical circuit diagram for a diamond filter is shown in FIG. 2g. A capacitance C6 is connected, together with several conductor loop windings, in this example 8, into an oscillating circuit. After four conductor loop windings 24d, which are connected in series, the connection is initially produced with the last conductor loop winding 24e. All remaining conductor loop windings 24f in series to the branching point are then connected to each other in series.

Production of a vessel filter in the variant of the diamond filter is shown in FIG. 3.

Figure 3A:
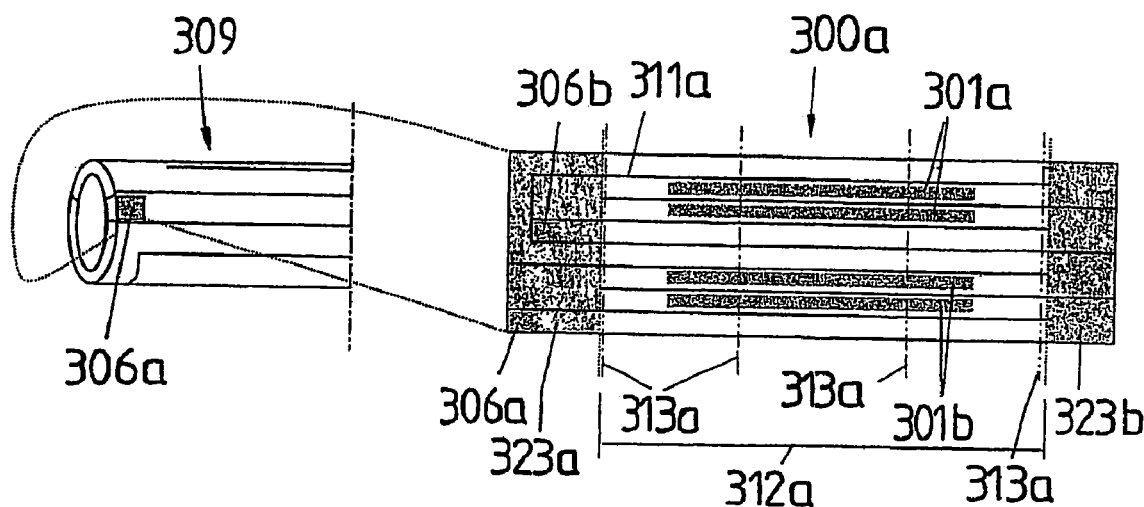
FIG. 3a shows a cutting pattern and a conductor track plan for production of a vessel filter from a Nitinol tube.

On the left of FIG. 3a, a Nitinol tube 309 with the depicted cutting pattern is shown. On the right, the corresponding cutting pattern 300a and the conductor track winding plan are shown in two dimensions. The Nitinol tube 309 is fastened laterally in the region of joining or mechanical fastening 323a, b. It is then cut along cutting lines 311a and then expanded by expansion of the middle region 312a of the cut Nitinol tube 309. The cutting pattern 300a permits production of the vessel filter from only one piece. The Nitinol tube 309 has two connections 306a, 306b for a capacitor (not shown).

The bending sites of the filter braces 313a are indicated. The conductor loop windings 301a, shown in pairs, should remain parallel with a spacing of about 1-5 mm after expansion.

Figure 3B:
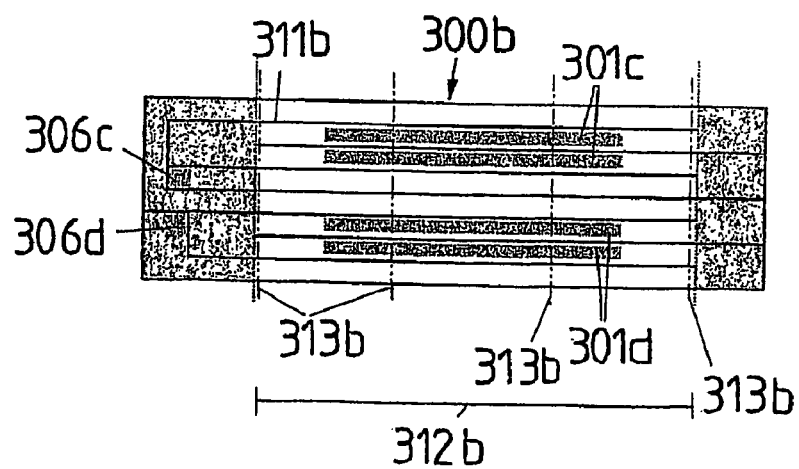
FIG. 3b shows an alternative cutting pattern and a conductor track winding plan for production of a vessel filter from a Nitinol tube.

FIG. 3b shows an alternative cutting pattern 300b or a conductor track winding plan for production of a vessel filter from a Nitinol tube. As already explained under FIG. 3a, the cutting lines 311b, the middle region 312b to be expanded and the bending sites 313b of the conductor loop are shown. In contrast to FIG. 3a, the connections 306c and 306d, on which a capacitor can be connected or formed, lie closer in FIG. 3b. Instead of an external capacitor, an insulation layer and a conductor layer on it can be applied on the capacitor connection surfaces 306c and 306d, which then has electrical contact with one end.

The right-half of a conductor track winding plan, similar to that of FIG. 3b, is shown in FIG. 3c. One possible cutting pattern is shown which increases the filter effect on at least one of the filter cages by the additionally spread-out filter braces 315a. V-shaped cuts 316a are then applied with a laser in two adjacent conductor loop windings 301d which, during bending, lead to additional braces 315 of the two conductor loop windings 301d.

FIG. 3d shows the expanded cross-sectional view of a vessel filter. The conductor loop windings 304 are divided and run as continuous parallel conductor loop windings 315a without mutually short-circuiting each other and threatening the function.

The additional braces 315a that are arranged only adjacent to the filter cages, improve the filter properties with respect to filtering of blood. The braces can belong to an additional coupled or combined resonance circuit.

The right-half of a conductor track winding plan, similar to that of FIG. 3b, is shown in FIG. 3e, as already in FIG. 3c. Another possible cutting pattern is shown that increases the filter effect on at least one of the filter cages by the additionally expanded filter braces (315b in FIG. 30. Additional longitudinal cuts 316b are made in the individual windings with a laser in two adjacent conductor loop windings 301e, parallel to the cuts that produce the conductor loop windings, but only in short sections adjacent to the filter cage ends. During bending, these cuts lead to additional braces of one conductor loop winding 304b.

FIG. 3f shows the expanded longitudinal side view of the cage from FIG. 3e. The conductor loop windings 315b, produced by the additional longitudinal cuts (316b in FIG. 3e), have an oval shape after expansion and improve the filter properties. They form by dividing the conductor loop winding 304b and later merge again in it. Round and angular forms are also conceivable. In an electrical respect, the expansions change the homogeneity of the fields in the filter so that the illumination in the MR image can be adjusted.

Figure 3G:
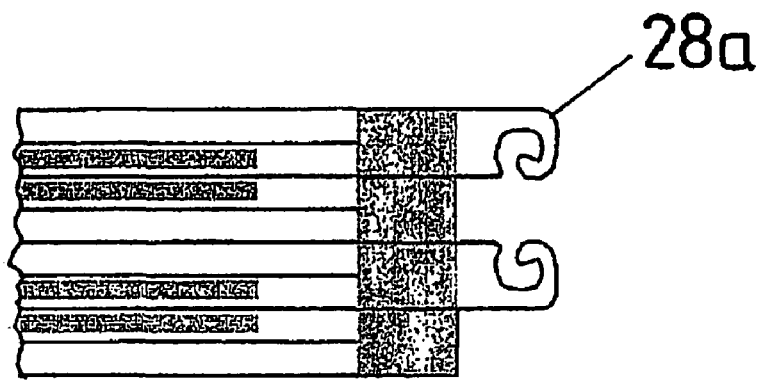
FIG. 3g schematically depicts a connection device applied to a cutting pattern.

A connection device 28a applied to the cutting pattern is shown in FIG. 3g. This connection device 28a serves for coupling with a device for introduction and/or to extraction of the filter. The connection device 28a consists of two hooks, offset by 180°, which are accessible from the same side. This connection device 28a permits the operator to easily handle the vessel filter during implantation and/or extraction. At the same time, the connection device 28a has the function of a braking device. By braking the filter during introduction into the blood vessel, the operator has greater manual control over the release process of the vessel filter from the catheter, which ultimately permits more precise implantation.

Figure 3H:
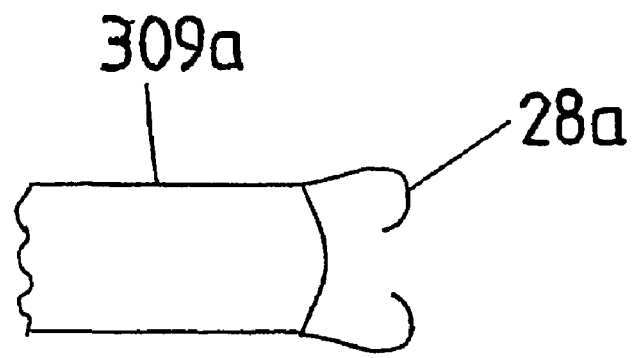
FIG. 3h shows a top view of a Nitinol tube with a connection device that can simultaneously assume the function of a braking device during the release process from the catheter.

FIG. 3h shows in a top view a Nitinol tube 309a, corresponding to the cutting pattern depicted in FIG. 3g. The two parts of the connection device 28a, arranged opposite each other, are slightly cambered outward and, because of this, are wider than the Nitinol tube 309a. When pushed out from the catheter, uncontrolled jumping out of the vessel filter by friction of the connection device on the catheter inside wall is prevented.

Figure 4B:
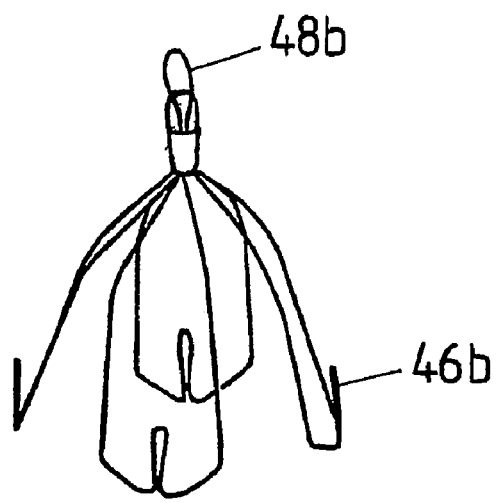
FIG. 4b shows a tulip filter with extensions that point in the direction of the filter tapering/blood stream.
Figure 4C:
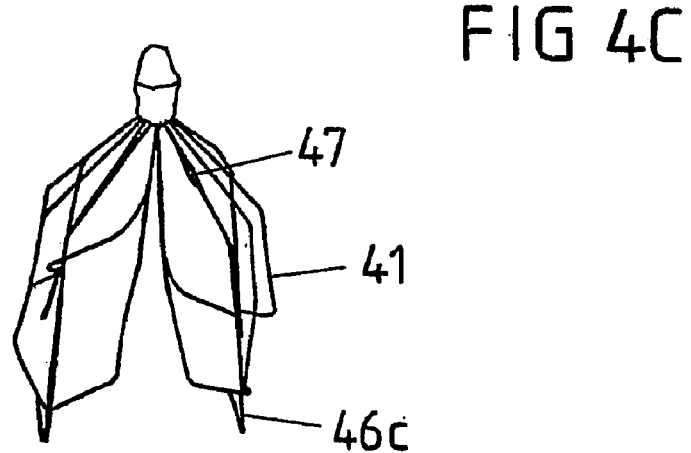
FIG. 4c shows a tulip filter with braces that are electrically separated from the oscillating circuit.

FIGS. 4a, 4b and 4c show variants of a so-called tulip filter 40. The conductor loop windings 44 in FIG. 4a are guided so that a tapering occurs on at least one longitudinal side, wherein extensions 46 are arranged on the side opposite the tapering. A situation is achieved, for example, by welding, in which said extensions 46 no longer have intermediate spaces. A connection device 48a, for introduction into and removal from the body, is shown. If this connection device is finally released from a catheter, via which the vein filter was introduced into the body, it simultaneously has the function of a braking device in order to prevent a jumping effect during release of the filter. Thus, the eye has the greatest diameter before deployment of the filter.

The extensions 46b shown in FIG. 4b are bent so that the ends point in the direction of filter tapering, i.e., in the direction of blood flow of the vessel in which the filter is arranged. Only these bent ends lie on the vessel wall. Because of this, the contact surface of the vessel filter with the vessel wall is minimized, and a situation is achieved in which the filter can be removed without rupturing the vessel wall since the intima grows around the extensions in pocket-like fashion. Anchoring in the vessel wall and intima of the vessel is achieved by this, which optimally counteracts the flow force of the blood. To remove the vessel filter, the filter is initially moved against the direction of blood flow in order to remove the extensions from the intima pockets. After collapse of the filter, it can be removed without problem from the body. A connection device 48b for introduction into and removal from the body is also shown which can again serve as a braking device during release.

In FIG. 4c, the extensions 46c are moveably arranged relative to conductor loop 41. In addition, braces 47 are arranged to fasten the filter cage and are electrically separated from the oscillating surface. The extensions are moveably arranged against the braces 47 of the tulip filter so that a change in resonance frequency by movement is compensated by a change in filter diameter. The resonance frequency remains essentially constant on this account.

Figure 4D:
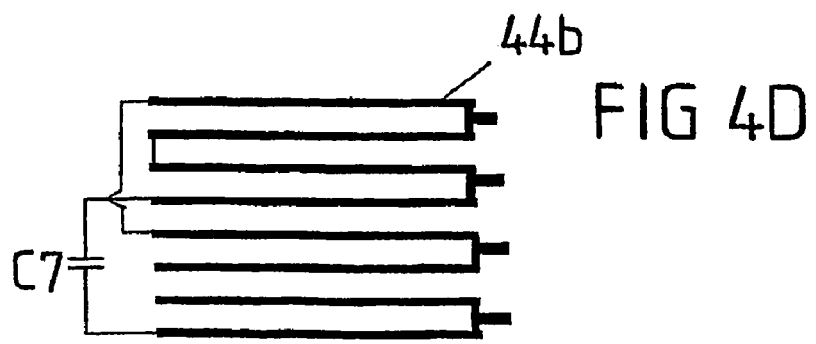
FIG. 4d shows a circuit diagram of a tulip filter for the vertical and horizontal MRT main magnetic field.

FIG. 4d shows the electrical circuit diagram of a tulip filter. A capacitance C7 is arranged together with four conductor loop windings 44b which are joined at one end.

Figure 5A:
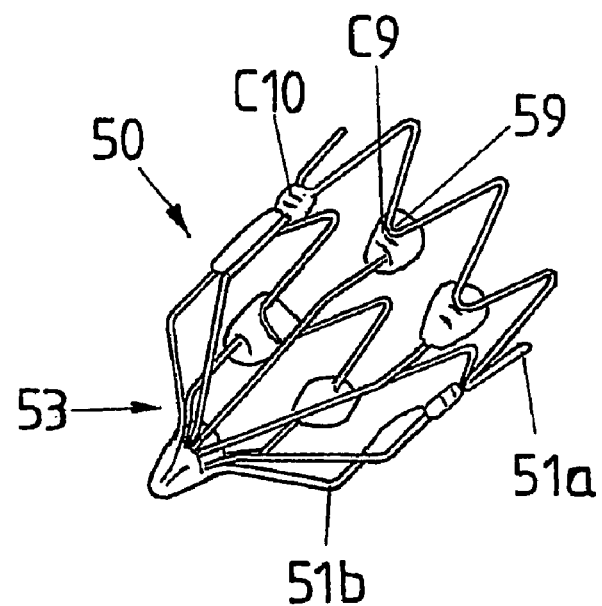
FIG. 5a shows a low-pass birdcage filter.

FIGS. 5a and b show different variants of a so-called birdcage filter 50.

FIG. 5a shows a low-pass birdcage filter with two conductor loops 51a, 51b, wherein only one of the conductor loops 51b is tapered on one side and forms a filter cage 53. Different capacitances are formed, for example, C9 and C10. The low-pass birdcage filter can also form two filter cages.

Figure 5B:
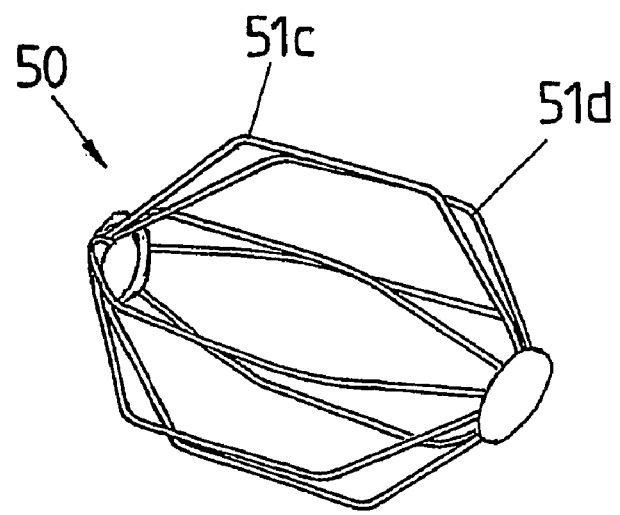
FIG. 5b shows a high-pass birdcage filter.
Figure 5C:
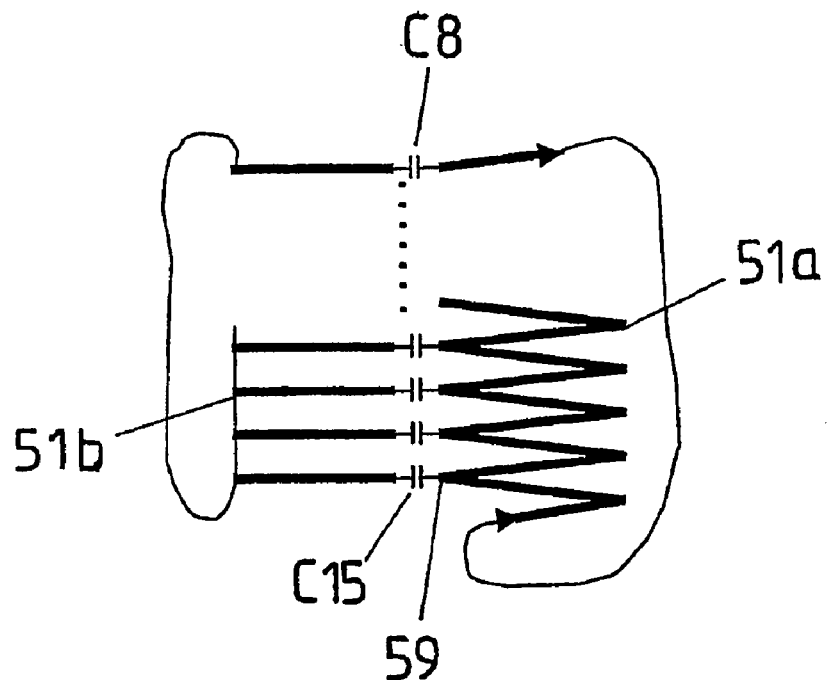
FIG. 5c shows a circuit diagram of a low-pass birdcage filter for the vertical and horizontal MRT main magnetic field.

FIG. 5c shows a circuit diagram for the low-pass birdcage filter according to FIG. 5a. The depicted variant contains two closed conductor loops 51a and 51b according to the "low-pass birdcage principle," of which one 51a is guided in a zigzag shape and therefore foldable (cf. also FIG. 5a). This conductor loop 51a, in one part of its reversal point 59, forms capacitances, for example, C8 and C15, with another conductor loop 51b or offers fastening possibilities for an external capacitance, which, however, can also be produced by layers of insulating material and a conducting layer.

FIG. 5b shows a high-pass birdcage filter that is tapered on both sides and forms a double-filter. In contrast to the diamond filter, the high-pass birdcage filter contains several conductor loops, for example, 51c and 51d, which form contact, via capacitances, with at least one additional conductor loop. The high-pass birdcage filter, however, can also form only one filter cage.

Figure 5D:
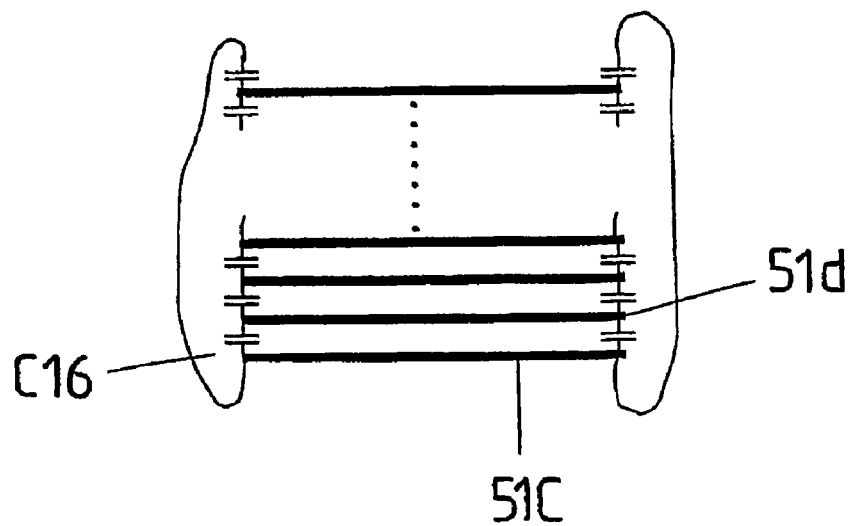
FIG. 5d shows a circuit diagram of a high-pass birdcage filter for the vertical and horizontal MRT main magnetic field.

FIG. 5d shows a circuit diagram for a high-pass birdcage filter containing several conductor loops 51c guided in the longitudinal direction of the vessel filter, each of which is connected on its ends via a capacitance (for example, C16) to another conductor loop 51d. Several oscillating circuits are then formed according to the "high-pass birdcage principle."

Figure 6A:
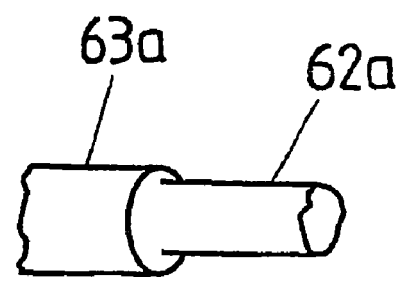
FIG. 6a shows a fixed coupling between the guide wire/catheter and vessel filter.
Figure 6B:
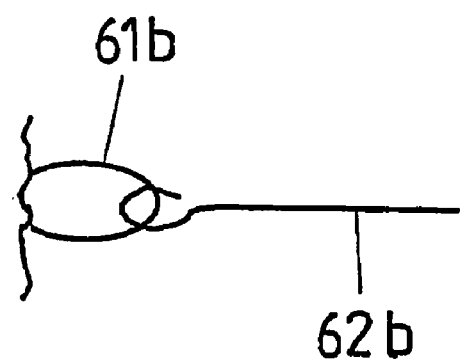
FIG. 6b shows a releasable coupling between the guide wire/catheter and vessel filter.
Figure 6C:
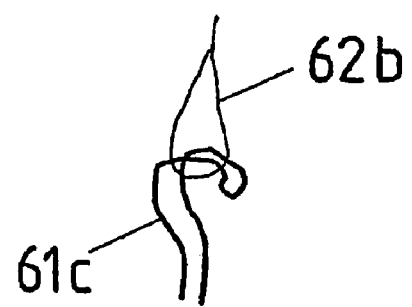
FIG. 6c shows a releasable coupling between the guide wire/catheter and vessel filter.

FIG. 6a-6c show possibilities for coupling between a guide wire/catheter, on the one hand, and a vessel filter, on the other. A fixed coupling between a guide wire or catheter 62a and a vessel filter 63a is shown in FIG. 6a: the guide wire or catheter 62a is then guided out of the vessel filter 63a.

FIGS. 6b and 6c, on the other hand, show examples of releasable mechanical couplings: the conductor loop 61b of the filter in FIG. 6b is then guided loop-like from the resonance circuit. A hook-like guide wire or end region of a catheter 62b can enclose the loops. As shown in FIG. 6c, it is also possible to form the loops from the guide wire/catheter 62c and the hooks from the conductor loop 61c.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

The invention claimed is:

1. A vessel filter for filtering solids in a liquid flowing through said vessel filter, said vessel filter designed for use with a magnetic resonance tomograph having an external magnetic field, said magnetic field having a tomograph frequency, said vessel filter comprising:
   a conductor having a first end and a second end, the entire length of said conductor bent into a shape that provides mechanical filtering and also creates an inductance, wherein said first end and said second end are proximate one another;
   a nonconductive dielectric positioned between said first end and said second end in order to prevent shorting between said first end and said second end, wherein a capacitance is thereby created by said first end, said nonconductive dielectric, and said second end, wherein said capacitance and said inductance form a series resonant circuit;
   wherein said capacitance and said inductance are chosen to have a resonant frequency tuned to said tomograph frequency;
   wherein the conductor forms solely the vessel filter and said filtering is solely performed by said conductor and nonconductive dielectric;
   wherein said ends of said conductor are insulated with an insulator that represents said dielectric and forms said capacitance with said ends separated by said insulator; and
   wherein said vessel filter is configured to be implanted within a vessel.

2. The vessel filter according to claim 1, wherein the conductor is covered with a nonconductive coating.

3. The vessel filter according to claim 2, wherein said nonconductive coating forms said nonconductive dielectric.

4. The vessel filter according to claim 1, wherein the conductor comprises at least one electrically nonconducting material on whose surface at least one conductive material is carried.

5. The vessel filter according to claim 1, wherein the conductor is unfoldable from a folded position.

6. The vessel filter according to claim 5, wherein the conductor is unfoldable during and/or after implantation in a body.

7. The vessel filter according to claim 1, wherein the conductor includes a plurality of conductor loop windings guided so that the greatest spacing of the conductor loop windings from each other is present in the center of the vessel filter and has a reduced spacing of the conductor loop windings from each other on at least one edge side.

8. The vessel filter according to claim 7, wherein the spacing of the conductor loops windings from each other is reduced toward multiple edge sides relative to the center of the vessel filter.

9. The vessel filter according to claim 7, wherein the conductor forms a double-filter in which the respective ends of the conductor loops each form a filter cage.

10. The vessel filter according to claim 7, wherein the vessel filter has at least one brace which is connected to the conductor loops.

11. The vessel filter according to claim 10, wherein said at least one brace is conducting and is conductively connected to said conductor loop.

12. The vessel filter according to claim 10, wherein said at least one brace is movably connected to individual conductor loop windings.

13. The vessel filter according to claim 10, wherein said at least one brace is made of bioresorbable material.

14. The vessel filter according to claim 7, wherein at least one conductor loop winding is provided with at least one hook for fastening in a vessel wall.

15. The vessel filter according to claim 1, wherein the conductor includes a plurality of conductor loop windings that merge on one side of the filter to form a filter cage and extend to the other side of the filter.

16. The vessel filter according to claim 1, wherein the conductor has at least one conductor loop winding forming at least one extension that serves for connection of the filter to a vessel wall.

17. The vessel filter according to claim 16, wherein adjacent regions of the conductor loop winding are spaced from each other by means of the at least one extension.

18. The vessel filter according to claim 16, wherein adjacent regions of the conductor loop winding are connected without intermediate space to each other in the at least one extension.

19. The vessel filter according to claim 16 which further includes at least one brace for fastening of the vessel filter, wherein said extension is moveably arranged relative to brace.

20. The vessel filter according to claim 1, wherein the conductor has individual windings that extend in a longitudinal direction of the vessel filter.

21. The vessel filter according to claim 1, wherein the conductor is formed from a single material piece.

22. The vessel filter according to claim 1, wherein the conductor is produced by repeated lengthwise cutting of a tube and then expansion.

23. The vessel filter according to claim 1, wherein the vessel filter has at least one connection device for coupling to a device for introduction and/or extraction of the filter.

24. The vessel filter according to claim 23, wherein the connection device is constructed and arranged so that it simultaneously creates a braking device for the braking of the filter during introduction into the body.

25. The vessel filter according to claim 1, wherein the vessel filter contains at least one connection device constructed and arranged for braking of the filter during introduction into the body.

26. A vessel filter for filtering solids in a liquid flowing through said vessel filter, said vessel filter designed for use with a magnetic resonance imaging tomograph having an external magnetic field, said magnetic field having a tomograph frequency, said vessel filter comprising:
  at least one conductor having a first end and a second end, the entire length of said conductor bent into a shape that provides mechanical filtering and also creates an inductance, wherein said first end and said second end are proximate one another; and
  at least one nonconductive dielectric positioned between said first end and said second end in order to prevent shorting between said first end and said second end, wherein a capacitance is thereby created by said first end, said nonconductive dielectric, and said second end, wherein said capacitance and said inductance form a series resonant circuit;
  wherein said capacitance and said inductance are chosen to have at least one resonant frequency tuned to said tomograph frequency;
  wherein the at least one conductor forms solely the vessel filter and said filtering is solely performed by said at least one conductor and said at least one nonconductive dielectric;
  wherein said ends of said at least one conductor are insulated with an insulator that represents said dielectric and forms said capacitance with said ends separated by said insulator; and
  wherein said vessel filter is configured to be implanted within a vessel.

27. A vessel filter for filtering solids in a liquid flowing through said vessel filter, said vessel filter designed for use with a magnetic resonance imaging tomograph having an external magnetic field, said magnetic field having a tomograph frequency, said vessel filter comprising:
  at least one conductor having a first end and a second end, the entire length of said conductor bent into a shape that provides mechanical filtering and also creates an inductance, wherein said first end and said second end are proximate one another; and
  at least one nonconductive dielectric positioned between said first end and said second end in order to prevent shorting between said first end and said second end, wherein a capacitance is thereby created by said first end, said nonconductive dielectric, and said second end, wherein said capacitance and said inductance form a series resonant circuit;
  wherein said capacitance and said inductance are chosen to have at least one resonant frequency tuned to said tomograph frequency;
  wherein the at least one conductor forms solely the vessel filter and said filtering is solely performed by said at least one conductor and said at least one nonconductive dielectric;
  wherein said inductance is created substantially as a result of said shape of said at least one conductor;
  wherein said ends of said at least one conductor are insulated with an insulator that represents said dielectric and forms said capacitance with said ends separated by said insulator; and
  wherein said vessel filter is configured to be implanted within a vessel.

28. A vessel filter for filtering solids in a liquid flowing through said vessel filter, said vessel filter designed for use with a magnetic resonance imaging tomograph having an external magnetic field, said magnetic field having a tomograph frequency, said vessel filter comprising:
  at least one conductor having a first end and a second end, the entire length of said conductor bent into a shape that provides mechanical filtering and also creates an inductance, wherein said first end and said second end are proximate one another; and
  at least one nonconductive dielectric positioned between said first end and said second end in order to prevent shorting between said first end and said second end, wherein a capacitance is thereby created by said first end, said nonconductive dielectric, and said second end, wherein said capacitance and said inductance form a series resonant circuit;
  wherein said capacitance and said inductance are chosen to have at least one resonant frequency tuned to said tomograph frequency; and
  wherein the at least one conductor forms solely the vessel filter and said filtering is solely performed by said at least one conductor and said at least one nonconductive dielectric;
  wherein said shape comprises a plurality of continuous radial loops, each one of said radial loops beginning from and returning to an area proximate said at least one nonconductive dielectric;
  wherein said ends of said at least one conductor are insulated with an insulator that represents said dielectric and forms said capacitance with said ends separated by said insulator; and
  wherein said vessel filter is configured to be implanted within a vessel.

* * * * *